United States Patent
Johansson et al.

(10) Patent No.: US 10,869,622 B2
(45) Date of Patent: Dec. 22, 2020

(54) BODY FLUID LEAKAGE DETECTION AQUEOUS COMPOSITION

(71) Applicants: MAGLE CHEMOSWED HOLDING AB, Malmö (SE); UNIVERSITÄT HEIDELBERG, Heidelberg (DE)

(72) Inventors: Henrik Johansson, Kristianstad (SE); Peter Schuisky, Tjörnarp (SE); Thomas Pausch, Heidelberg (DE); Thilo Hackert, Heidelberg (DE)

(73) Assignees: MAGLE CHEMOSWED HOLDING AB, Malmö (SE); UNIVERSITÄT HEIDELBERG, Heidelberg (DE)

( * ) Notice: Subject to any disclaimer, the term of this patent is extended or adjusted under 35 U.S.C. 154(b) by 0 days.

(21) Appl. No.: 16/478,629

(22) PCT Filed: Dec. 20, 2018

(86) PCT No.: PCT/EP2018/086183
§ 371 (c)(1),
(2) Date: Jul. 17, 2019

(87) PCT Pub. No.: WO2019/122120
PCT Pub. Date: Jun. 27, 2019

(65) Prior Publication Data
US 2019/0343435 A1    Nov. 14, 2019

(30) Foreign Application Priority Data
Dec. 20, 2017    (EP) ..................................... 17208850

(51) Int. Cl.
*A61B 17/06*    (2006.01)
*A61B 5/145*    (2006.01)
(Continued)

(52) U.S. Cl.
CPC ........ *A61B 5/14539* (2013.01); *A61B 5/1473* (2013.01); *A61B 17/0644* (2013.01); *A61B 17/06166* (2013.01); *A61K 49/006* (2013.01)

(58) Field of Classification Search
CPC  A61K 49/00; A61K 49/006; A61B 17/06166; A61B 17/0644; A61B 5/14539; A61B 5/1473
(Continued)

(56) References Cited

U.S. PATENT DOCUMENTS

2008/0319101 A1*  12/2008  Nakajima ............. A61L 24/043
                                                           523/111
2010/0136707 A1    6/2010  Kritzman et al.

FOREIGN PATENT DOCUMENTS

CN    105203541 A    12/2015
CN    105334209 A    2/2016
(Continued)

OTHER PUBLICATIONS

International Search Report and Written Opinion for PCT/EP2018/086183 dated Mar. 18, 2019.
(Continued)

*Primary Examiner* — Christine T Mui
(74) *Attorney, Agent, or Firm* — Renner, Otto, Boisselle & Sklar, LLP (57) ABSTRACT

A body fluid leakage detection aqueous composition, for use e.g. in intraoperative pancreatic fluid leakage detection. The composition comprises a gelling agent, increasing the viscosity of the composition, and buffering species, the composition thereby being buffered. The gelling agent is cross-linked α-glucan microspheres. Further, the composition comprises a pH-indicator. The pH of the composition is at least 0.1 pH units lower, or higher, than a pKa of the pH-indicator.

20 Claims, 3 Drawing Sheets

(51) Int. Cl.
*A61B 5/1473* (2006.01)
*A61B 17/064* (2006.01)
*A61K 49/00* (2006.01)

(58) Field of Classification Search
USPC .......................................................... 436/64
See application file for complete search history.

(56) References Cited

FOREIGN PATENT DOCUMENTS

| EP | 2857830 A1 | 4/2015 |
| --- | --- | --- |
| FR | 2902322 A1 | 12/2007 |
| WO | 2012073132 A1 | 6/2012 |

OTHER PUBLICATIONS

Mori, et al., Intraoperative Visualization of Pancreatic Juice Leaking From the Pancreatic Stump in a Swine Model, Gastroenterology in Motion, (2015; 149: p. 1334 to 1336).
D. R. Lu, et al., Starch-based completely biodegradable polymer materials, eXPRESS Polymer Letters vol. 3, No. 6 (2009) p. 366-375.
Patrícia B. Malafaya et al., Starch-based microspheres produced by emulsion crosslinking with a potential media dependent responsive behavior to be used as drug delivery carriers, J. Mater. Sci: Mater Med (2006), 17:371-377.
Koji Yamaguchi, Litmus Paper Helps Detect Potential Pancreatoenterostomy Leakage, The American Journal of Surgery vol. 175 Mar. 1998 p. 227-228.

\* cited by examiner

BODY FLUID LEAKAGE DETECTION AQUEOUS COMPOSITION

This application is a national phase of International Application No. PCT/EP2018/086183 filed Dec. 20, 2018 and published in the English language, which claims priority to European Application No. 17208850.2 filed Dec. 20, 2017, both of which are hereby incorporated by reference.

FIELD OF THE INVENTION

The present invention relates to a body fluid leakage detection composition and to its use in detecting pancreatic fluid leakage in conjunction with pancreas surgery, e.g. partial pancreatectomy.

BACKGROUND

Pancreatic cancer is the fourth leading cause of cancer-related death in the world, with pancreatic resection the only potential cure. Tens of thousands of these procedures are performed worldwide yearly. A frequent, serious, and expensive complication is postoperative pancreatic fistula caused by pancreatic fluid leakage, the most important unsolved problem of pancreatic surgery. Leakage of pancreatic fluid pose not only a risk of bacterial infections, but also of proximate organs like the intestine or blood vessels being digested by a self-digestion action of the pancreatic fluid, which may cause serious bleeding and even death.

Therefore, pancreatic fluid leakage is of the most important morbidity issues in pancreatectomies. Although various pancreatectomy techniques of pancreatic dissection and closure as well as postoperative management techniques have been studied, pancreatic fluid leakage still occurs at a frequency of 30% to 50%. Because every case of postoperative pancreatic fistula is potentially life-threatening, early detection is vital. The difficulty with pancreatic fluid leakage is that the leakage is macroscopically imperceptible, and currently surgeons cannot see if and where the pancreatic remnant is leaking during pancreatic operations. Existing intraoperative approaches to prevent or close pancreatic fluid leakage are therefore imprecise because no reliable and feasible methods allowing visualization of pancreatic fluid leakage are in clinical use.

During partial pancreatectomiy is it difficult to prevent pancreatic fluid leakage completely, as openings of the pancreatic ductal system at the pancreatic tissue cut surface are small and hardly visible thus targeted closure is difficult to conduct. Furthermore, the pancreatic tissue is very soft so surgical closure of leakage must be very gentle in order to avoid ruptures.

Measurement of the concentration of amylase, which is a glycolytic enzyme, in intraperitoneal drainage fluid is currently used as an indirect method of detecting pancreatic fluid leakage after partial pancreatectomies. However, this technique suffers from being indirect and not allowing for direct detection and localization of pancreatic fluid leakage during pancreatic surgery. It would thus be desired to provide a technique which can visualize and localize leakage of colorless and transparent pancreatic fluid already during the operation.

EP 2 857 830, and the related publication by Mori et al in Gastroenterology (cf. 2015; 149: p. 1334 to 1336), discloses a fluorescent probe stated to be capable of rapidly detecting and imaging the presence of leakage of pancreatic fluid during or after surgery. Though stated to be able to provide rapid detection and imaging with high sensitivity, the probe still suffers from requiring UV-light illumination and use of light-blocking glasses in order to imaging leakage. In addition, the chemical reactions eventually resulting in leakage visualization, take minutes before the leakage is visualized thus disturbing the "surgical flow of progress" remarkably. Further, as generally known, fluorescent probes tend to have potentially toxic side effects and UV-radiation can lead to damaging of DNA. Thus, the provided visualization approach is rather complex, inefficient and unsafe to be implemented at hospitals. Further, the dosage form used suffers from being a bit imprecise, i.e. the exact point of leakage may be hard to localize.

CN105334209 and CN105203541 disclose a pancreatic juice developer. The pancreatic juice developer comprises an acid-base indication compound, e.g. thymol blue and bromothymol blue. The pancreatic juice developer is provided in various dosage forms selected from the group consisting of lotion, spray, indicator paper, indicated gauze, cotton and a cotton swab. Similar to the fluorescent probe of EP 2 857 830, these pancreatic juice developers suffer from being imprecise, i.e. the exact point of leakage may be hard to identify, and from requiring removal of the dosage form once used.

Given the difficulty in carrying out a targeted treatment on pancreatic tissue, rapid and precise localization of the exact point of leakage would be highly desired. Further, it would be desired to provide a degradable visualization means, which enables repeated application to re-check sufficient closure and which does not need to be removed at the end of the operation. Furthermore, it would also be desired to provide visualization means for detecting pancreatic fluid leakage in laparoscopic surgery.

SUMMARY

Consequently, the present invention seeks to mitigate, alleviate, eliminate or circumvent one or more of the above-identified deficiencies in the art and disadvantages singly or in any combination by providing, according to a first aspect of the invention, a body fluid leakage detection aqueous composition, the composition comprising a gelling agent, increasing the viscosity of the composition, and buffering species, the composition thereby being buffered. The gelling agent is cross-linked α-glucan microspheres. The composition further comprises a pH-indicator. The pH of the composition is at least 0.1 pH units lower, or higher, than a pKa of the pH-indicator.

According to an embodiment, the gelling agent is cross-linked starch microspheres. The composition may thus comprise 5 to 25 wt % cross-linked starch microspheres, preferably 10 to 20 wt % cross-linked starch microspheres, more preferably 13 to 17 wt % cross-linked starch microspheres. The degree of cross-linking, expressed as the weight ratio cross-linker:starch, may be in the range 12 to 20 wt %, such as in the range 13.5 to 18.5 wt %, or 15.0 to 17.0 wt %. According to an alternative embodiment, the gelling agent is cross-linked dextran microspheres.

A pKa of the pH-indicator may be in the range 5 to 9; preferably in the range 6 to 8; more preferably in the range 6.5 to 7.5. The pH-indicator may thus be bromothymol blue and the composition may comprise 0.001 to 0.5 wt %, such as 0.005 to 0.25 wt % or 0.01 to 0.1 wt %, bromothymol blue. Further, the pH of the composition may be between 4 and 7; preferably between 5 and 6. The buffering species present in the composition to provide a buffered composition may be present in an amount of 0.1 to 30 mM, preferably 0.5 to 10 mM, more preferably 1.0 to 5 mM.

According to preferred aspect of the invention, the body fluid leakage detection aqueous is a pancreatic fluid leakage detection aqueous composition. The pH of the such a pancreatic fluid leakage detection aqueous composition is in the range 4 to 6 and a pKa of the pH-indicator is in the range 6 to 8; preferably in the range 6.5 to 7.5.

According to another aspect of the invention there is provided such a pancreatic fluid leakage detection aqueous composition for use in detecting pancreatic fluid leakage in conjunction with pancreatic surgery, e.g. partial pancreatectomy.

According to another aspect of the invention there is provided a method for detecting pancreatic fluid leakage in conjunction with pancreatic surgery. The method comprises:
applying to the pancreatic fluid leakage detection aqueous composition; and
detecting and localizing any leakage of pancreatic fluid on the tissue surface of the pancreas by a change in color of the pancreatic fluid leakage detection aqueous composition.

Further advantageous features of the invention are defined in the dependent claims. In addition, advantageous features of the invention are elaborated in embodiments disclosed herein.

DETAILED DESCRIPTION

In order to provide a pancreatic fluid leakage detection means, addressing needs in the art, various concepts were considered. It was found that powder based means, e.g. indicator impregnated cross-linked starch microspheres, suffered from being difficult to handle and apply. Further, the applied powder was easily flushed away by pancreas juice, thus providing imprecise detection, if any. Further, neither attempts to overcome the shortcomings of dry powders by providing them on a tape or replacing them with paper wipers or gauze impregnated with indicator was successful and failed to provide precise detection.

In order to overcome these shortcomings and to provide a pancreatic fluid leakage detection means addressing needs in the art, a fluid, rather than dry, solid, or immobilized, pancreatic fluid leakage detection means was then considered. Thus, a body fluid leakage detection aqueous composition comprising a leakage indicator was provided.

It was recognized that employing a pH-indicator as leakage indicator provides quick response in to change in pH caused by leakage of pancreatic fluid, provided that the pH of the composition differs from a pKa of the pH-indicator such that a change in pH results in the pH-indicator changing color. The pH of pancreatic fluid is higher (about 8.3 to 8.5) than the pH of the normal interstitial fluid (pH about 7.4). By use of suitable pH-indicator, e.g. bromothymol blue, pancreatic fluid leakage may be detected. Further, not only should the pH of the composition differ from a pKa of the pH-indicator. It was also seen that the composition should comprise buffering species in order to provide a buffered composition. The buffer will allow for improved contrast between positive and negative detection.

Further, in order to provide the body fluid leakage detection aqueous composition with improved precision, the viscosity of the aqueous composition needs to be increased. As an example, application of a pH-indicator dissolved in water, e.g. by spraying, did not provide any precise detection. It was however found that adding a gelling agent increased the viscosity in a desirable manner to provide for a sharp border between positive and negative detection. Increasing the viscosity of the composition will decrease diffusion within the composition, being present as a gel, or a semi-solid mass. Decreased diffusion within the composition implies that a pH change due to leaking pancreatic fluid causing a shift in color of the composition (bromothymol blue shifts from yellow to blue in the pH-range 6.0 to 7.6) will be more localized and hence the precision improved. Thus, the precision of a body fluid leakage detection aqueous composition may be improved by adding a gelling agent increasing the viscosity of the composition.

According to an embodiment there is thus provided a body fluid leakage detection aqueous composition comprising a gelling agent in the form of cross-linked α-glucan microspheres. The composition further comprises a pH-indicator. In order to provide a visible color change in response to a change in pH, the pH of the composition is at least 0.1 pH units lower, or higher, than a pKa of the pH-indicator.

As an example, for bromothymol blue having a pKa of 7.0, the pH of the composition should be 6.9 or lower, or 7.1 or higher. In order provide a more clear color change the pH of the composition may be at least 0.2, 0.3, 0.4, 0.5, 0.6, 0.7, 0.8, 0.9, or 1.0, pH units lower, or higher, than a pKa of the pH-indicator. According to an embodiment, the pH of the composition is at least 1.0, pH units lower, or higher, than a pKa of the pH-indicator.

For detection of leakage of pancreatic fluid, the pH of the composition is preferably lower than a pKa of the pH-indicator, as the pH of interstitial fluid is lower than the pH of pancreatic fluid. Thus, the pH of the composition may be at least 0.2, 0.3, 0.4, 0.5, 0.6, 0.7, 0.8, 0.9, or 1.0, pH units lower than a pKa of the pH-indicator. According to an embodiment, the pH of the composition is at least 1.0, pH units lower than a pKa of the pH-indicator.

Further, it was found to be necessary for the composition to comprise buffering species, i.e. the composition should be buffered. According to an embodiment, the composition thus is buffered. The buffering species may be present in an overall amount of 0.1 to 30 mM, such as 0.5 to 10 mM or 1.0 to 5 mM. Having a too high concentration of buffering species may result in no, or delayed, color change. Delayed color change will not only suffer from delayed indication, but also decreased precision. Further, a too low concentration of buffering species may result in imprecise leakage detection and potentially even in false positives.

Buffering the composition provides a more robust body fluid leakage detection aqueous composition. Further, interstitial fluid and pancreatic fluid not only differ in pH, but also in buffer strength. Whereas the interstitial fluid not significantly will change the pH of a buffered composition, pancreatic fluid, having higher buffer strength due to the high concentrations of bicarbonate in pancreatic fluid, will be able to increase the pH also of a buffered body fluid leakage detection aqueous composition and thereby having the body fluid leakage detection aqueous composition changing color. Pancreatic fluid comprise high concentrations of bicarbonate in order to be able to neutralize acidic gastric acid. Thus, buffering the body fluid leakage detection aqueous composition may be advantageous to further improve the precision of the composition.

As recognized by the skilled person, various buffering systems may be used to provide a buffered composition. As already outlined, the buffered composition may have a pH of 4 to 7, such as 5 to 7, 5 to 6, or 6 to 7. The composition may thus comprise phosphate-buffered saline (PBS). According to an embodiment, the composition is phosphate and/or citrate buffered. The composition may comprises 0.1 to 30 mM phosphate, such as 0.5 to 10 mM or 1.0 to 5 mM phosphate. In this context, the phosphate concentration refers to the overall concentration of various phosphate species (e.g. $HPO_4^{2-}$ and $H_2PO_4^-$).

Further, the buffering species may be based on a compound selected from the group consisting of phosphoric acid, citric acid, acetic acid, lactic acid, PIPES (piperazine-N,N'-bis(2-ethanesulfonic acid)), MES (2-(N-morpholino) ethanesulfonic acid) or a mixture of one or several of these compounds. It is however preferred, that the buffering species are be based on endogenous compound(s), e.g. phosphoric acid, citric acid, acetic acid and/or lactic acid.

Depending on the pH-indicator, the present composition may be used to detect leakage of various kinds of body fluids, e.g. bile, similar to pancreatic fluid being weakly alkaline, or gastric juice, being acidic. Bile is secreted by the gale bladder. Thus, the present body fluid leakage detection aqueous composition may also be used in detecting leakage of bile, e.g. after trauma or in conjunction with gale bladder surgery. While not limited thereto, a pKa of the pH-indicator may be in the range 5 to 9; preferably in the range 6 to 8; more preferably in the range 6.5 to 7.5. For detection of leakage of pancreatic fluid, a pKa in the range 6 to 8, preferably in the range 6.5 to 7.5, was found to be suitable. This range is preferred also for detection of leakage of bile. According to an embodiment, the pH-indicator is bromothymol blue. Not only does bromothymol blue have a proper pKa, but bromothymol blue does also exhibits a sharp color contrast between low (yellow) and high (dark blue) pH. Furthermore, also the contrast between the indication (dark blue) and tissue and blood is sharp. Further, the pH-indicator may be phenol red (3-Amino-7-dimethylamino-2-methylphenazine hydrochloride) or neutral red (also known as phenolsulfonphthalein or 3,3-Bis(p-hydroxyphenyl)-2,1-3H-benzoxathiole 1,1-dioxide).

For detection of leakage of gastric juice, a pKa of the pH-indicator may be in the range 4 to 6. As recognized by the skilled person a number of pH-indicators having a pKa in this range, and hence a corresponding color change, are known. As an example, the pH-indicators bromocresol green (2,6-Dibromo-4-[7-(3,5-dibromo-4-hydroxy-2-methyl-phenyl)-9,9-dioxo-8-oxa-9,6-thiabicyclo[4.3.0]nona-1,3,5-trien-7-yl]-3-methyl-phenol), methyl red (2-{[4-(Dimethylamino)phenyl]diazenyl}benzoic acid), and methyl purple (CAS Registry Number: 1340-02-9) may be mentioned.

As already mentioned, the pH of the composition should differ from the pKa of the pH-indicator. The pH of the composition may be between 4 and 7, preferably between 5 and 6. A slightly acidic pH was found to be beneficial in detecting leakage of pancreatic fluid.

As already discussed, the body fluid leakage detection aqueous composition comprises a gelling agent in the form of cross-linked α-glucan microspheres to increase the viscosity of the composition. A composition with increased viscosity has improved precision, i.e. the color change only appears to close to the leakage when applied to e.g. the pancreatic remnant after pancreatectomy. It is to be noted though, that while increasing the viscosity of the composition improves the precision, it may also slower the color change. While a more viscous composition may provide a more precise leakage localization, a too viscous composition may suffer from changing color slowly in response to leakage. Further, a too thin or too viscous composition may be harder to apply.

It is preferred if the composition is markedly shear thinning and/or Bingham (pseudo)plastic. A composition being shear thinning and/or Bingham (pseudo)plastic will remain in position once applied and not spread. Still, the composition can easily be applied via e.g. a syringe, given its shear thinning properties (cf. the "ketchup effect").

According to an embodiment, the body fluid leakage detection aqueous composition comprises 5 to 25 wt %, such as 10 to 20 wt %, 13 to 17 wt %, or 14 to 16 wt %, of the gelling agent. As outlined below, cross-linked starch microspheres represent a preferred gelling agent.

Not only the concentration of the gelling agent, but also the salt concentration, i.e. the ion strength, affects the viscosity of the composition. An increase in the strength in the solution has a decreasing effect on the viscosity. Concentrations higher than 1 M have a significant effect on viscosity. The decrease is caused by an ion-pairing between the charged ions and the macromolecules in the matrix. The introduction of ions leads at lower concentrations to a decreased attractive interaction among the macromolecules (biopolymers) due to the in-salting effect.

According to an embodiment, the ion strength in the body fluid leakage detection aqueous composition is 50 to 500 mM, such as 100 to 250 mM or 125 to 175 mM. An ion strength in the range 100 to 250 mM, such as 125 to 175 mM, may be especially preferred if the gelling agent is cross-linked starch microspheres.

It was found that the gelling agent preferably is cross-linked polysaccharide microspheres, such as cross-linked α-D-glucose-polymer (i.e. α-glucan) microspheres, e.g. cross-linked starch microspheres, or cross-linked dextran microspheres. Cross-linked polysaccharide microspheres, e.g. cross-linked starch microspheres, provides a composition being shear thinning and/or Bingham (pseudo)plastic. As already outlined, a composition being shear thinning and/or Bingham (pseudo)plastic will remain in position once applied and not spread. Still, the composition can easily be applied via e.g. a syringe, given its sheer thinning properties (cf. the "ketchup effect").

Further, by use of cross-linked polysaccharide microspheres, e.g. cross-linked starch microspheres, as the gelling agent, it was found to be easier to establish a composition of the body fluid leakage detection aqueous composition to obtain a viscosity suitable for body fluid leakage detection. Swollen microspheres improve the internal friction of the body fluid leakage detection aqueous composition. This gives that the consistency of the body fluid leakage detection aqueous composition is such that it becomes much easier to handle and apply. Furthermore, it also promotes the action of the indicator in the sense that color indication becomes more precise on location.

Furthermore, starch and cross-linked starch microspheres are bio-degradable. This implies, that a body fluid leakage detection aqueous composition comprising starch or cross-linked starch microspheres or a related gelling agent, as the gelling does not need to be removed but will be degraded in situ. The cross-linking, however implies that the cross-linked starch microspheres are more slowly degraded than native starch. Given the high concentration of amylase in pancreatic juice, the degradation of the gelling agent may be too rapid, if the gelling agent is starch not having been cross-linked.

As an alternative to cross-linked starch microspheres, cross-linked dextran microspheres may be used as gelling agent. Dextran mainly differs from starch by being branched by α-1,3 linkages. As dextran shows a highly branched structure and a different distribution of glycosidic linkages it cannot be degraded by α-amylase, or is only partially degraded by α-amylase. Most of dextran administered to the human body parentally is thus excreted by the kidney, rather than being degraded to glucose by α-amylase. However, some cells within the human body are able to degrade dextran to glucose.

According to an alternative embodiment, the gelling agent is cross-linked dextran microspheres. Given the resistance to degradation by α-amylase, cross-linked dextran microspheres may provide more persistent leakage detection than cross-linked starch microspheres. As dextran already is used clinically in e.g. intravenous solutions as volume expanders and as means of parenteral nutrition, the limited α-amylase degradation is not considered unacceptable for the present use as gelling agent in the present body fluid leakage detection aqueous composition. For some applications, use of cross-linked dextran microspheres as gelling agent may even be preferred.

According to an embodiment, the gelling agent is cross-linked starch microspheres. Cross-linked starch microspheres consist of starch of plant origin (e.g. potatoes) being cross-linked to provide microspheres. As recognized by the skilled person, starch is a natural polymer, which is constructed by a mixture of two polymeric chains, a branched glucose polymer (α-4-glucose chains with α6 branches). It is a natural material found in plants and animals where it functions as an energy store. The polymer consists of amylose (long chained and low-branched) and amylopectin (highly branched and short chained). The ratio between these two polymers is different depending on the source. As known in the art, degradable cross-linked starch microspheres (DSM) are formed by an emulsification process in which the polymer chains are cross-linked into the spherical shape. Microparticles of starch or modified starch have been shown in prior art (e.g. D. R. Lu et al *"Starch-based completely biodegradable polymer materials"* eXPRESS polymer Letters Vol. 3 No. 6 (2009) p. 366-375; P. B. Malafaya et al. *"Starch-based microspheres produced by emulsion crosslinking with a potential media dependent responsive behavior to be used as drug delivery carriers"* J. Mater. Sci: Mater Med (2006), 17:371-377). In the art, cross-linked starch microspheres are well-known as forming part of degradable drug delivery systems. The starch in the cross-linked starch microspheres may be hydrolyzed starch. The degree of hydrolyzation may be used to tune properties of the resulting cross-linked starch microspheres.

In cross-linking starch to provide cross-linked starch microspheres a cross-linker, e.g. epichlorohydrin, is used. According to an embodiment, the gelling agent is cross-linked starch microspheres that has been cross-linked by use of epichlorohydrin.

Cross-linked dextran microspheres may be obtained in a corresponding manner.

As the amylase levels in the pancreatic fluid is substantially higher than the normal levels in the body the degradation time of the starch based microspheres will be respectively shorten too.

The degree of cross-linking affects the resistance to degradation by amylase. Higher degree of cross-linking provides higher resistance to degradation. The degree of cross-linking should preferably be such that the cross-linked starch microspheres are intact for at least 5 minutes, when exposed to the body fluid to be detected, in order to allow for detecting any leakage with sufficient precession. A too high degree of cross-linking will however negatively affect the properties, e.g. viscosity and detection time, of the composition According to an embodiment, the degree of cross-linking, expressed as the weight ratio cross-linker:starch, should be in the range 12 to 20 wt %, such as 13.5 to 18.5 wt %, or 15.0 to 17.0 wt %. For detection of pancreatic fluid, a cross linking degree of about 25 wt % was deemed to be preferred. The same ranges apply to cross-linked dextran microspheres.

The cross-linked starch microspheres are degraded in vivo by plasma amylase into oligosaccharides, maltose and eventually to glucose that enter the normal metabolism.

As the body fluid leakage detection aqueous composition is to be used in abdominal cavity when used as a pancreatic fluid leakage detection aqueous composition, the gelling agent should preferably be bio-degradable. Using a bio-degradable gelling agent implies that the gelling agent not necessarily must be completely removed before closing the abdominal cavity. Especially when to be used in laparoscopic surgery, it is advantageous, or even nearly necessary, that the gelling agent is bio-degradable. Cross-linked, starch microspheres represent a preferred example of a gelling agent being bio-degradable.

Cross-linked starch microspheres, as well as cross-linked dextran microspheres, may be provided in various sizes and may have various size-distribution. The figures provided below relates to cross-linked starch microspheres in swollen state as present within the body fluid leakage detection aqueous composition. The same ranges are applicable to cross-linked dextran microspheres. It was found that the cross-linked starch microspheres, or cross-linked dextran microspheres, should not be too small in order to exhibit markedly shear thinning and/or Bingham (pseudo)plastic properties. According to an embodiment, the volume based mean diameter (D[4,3]), as determined in accordance with ISO 13 320:2009 by using laser diffraction, thus is 100 to 1000 μm, such as 250 to 750 μm. Further, the volume based median diameter D[v, 0.5], as determined in accordance with ISO 13 320:2009, will typically be slightly lower than the volume based mean diameter. Still, also the volume median diameter D[v, 0.5], as determined in accordance with ISO 13 320:2009, may be in the range 100 to 1000 μm, such as in the range 250 to 750 μm, though being lower than the volume based median diameter. Further, the size-distribution may be such that 90% of the particles, as determined in accordance with ISO 13 320:2009, have a volume based diameter (D[v, 0.9]) of less than 300 to 2000 μm, such as less than 500 to 1500 μm. Further, the size-distribution may be such that 10% of the particles of the particles, as determined in accordance with ISO 13 320:2009, have a volume based diameter (D[v, 0.1]) of less than 50 to 600 μm, such as less than 100 to 500 μm, i.e. 90% of the particles having a diameter of at least 50 to 600 μm, such as at least 100 to 500 μm.

According to an embodiment, the size-distribution of the cross-linked starch microspheres, as present within the body fluid leakage detection aqueous composition, is such that:
 the volume based mean diameter D[4,3], as determined in accordance with ISO 13 320:2009 by using laser diffraction, is 100 to 1000 μm, such as 250 to 750 am; and/or
 the volume based diameter D[v, 0.9], as determined in accordance with ISO 13 320:2009 by using laser diffraction, is 300 to 2000 μm, such as 500 to 1500 am; and/or
 the volume based diameter D[v, 0.1], as determined in accordance with ISO 13 320:2009 by using laser diffraction, is 50 to 600 μm, such as 100 to 500 μm.

The type and amount of gelling agent in the body fluid leakage detection aqueous composition will affect the viscosity of the composition. According to an embodiment, the body fluid leakage detection aqueous composition comprises:
- 5 to 25 wt %, such as 10 to 20 wt %, 13 to 17 wt %, or 14 to 16 wt %, of the gelling agent, e.g. cross-linked starch microspheres;
- 0.001 to 0.5 wt %, such as 0.005 to 0.25 wt % or 0.01 to 0.1 wt %, of the pH-indicator, e.g. bromothymol blue; and
- at least 75 wt %, such as at least 80 wt %, water.

Preferably, the cross-linked starch microspheres in such an embodiment has a degree of cross-linking of 12 to 20 wt %, such as 13.5 to 18.5 wt %, or 15.0 to 17.0 wt %. Further, the concentration of the buffer may be 0.1 to 30 mM, such as 0.5 to 10 mM or 1.0 to 5 mM. The buffer may be a phosphate buffer. Further, the body fluid leakage detection aqueous composition may be saline based. Preferably, the aqueous composition comprises phosphate buffered saline in order to provide a buffered, isotonic composition. The ion strength of the body fluid leakage detection aqueous composition may according to this embodiment be 100 to 200 mM, preferably 125 to 175 mM.

Preferred, aspects (cross-linking, size, etc.) provided herein above in relation to cross-linked starch microspheres are equally applicable to cross-linked dextran microspheres. Thus, according to an embodiment, the volume based mean diameter (D[4,3]) of the cross-linked dextran microspheres, as determined in accordance with ISO 13 320:2009 by using laser diffraction, is 100 to 1000 µm, such as 250 to 750 µm. Further, the volume based median diameter D[v, 0.5], as determined in accordance with ISO 13 320:2009, will typically be slightly lower than the volume based mean diameter. Still, also the volume median diameter D[v, 0.5], as determined in accordance with ISO 13 320:2009, may be in the range 100 to 1000 µm, such as in the range 250 to 750 µm, though being lower than the volume based median diameter. Further, the size-distribution may be such that 90% of the particles, as determined in accordance with ISO 13 320:2009, have a volume based diameter (D[v, 0.9]) of less than 300 to 2000 µm, such as less than 500 to 1500 µm. Further, the size-distribution may be such that 10% of the particles of the particles, as determined in accordance with ISO 13 320:2009, have a volume based diameter (D[v, 0.1]) of less than 50 to 600 µm, such as less than 100 to 500 µm, i.e. 90% of the particles having a diameter of at least 50 to 600 µm, such as at least 100 to 500 µm. Further, according to an embodiment, the degree of cross-linking of the cross-linked dextran microspheres, expressed as the weight ratio cross-linker:dextran, should be in the range 12 to 20 wt %, such as 13.5 to 18.5 wt %, or 15.0 to 17.0 wt %. For detection of pancreatic fluid, a cross linking degree of about 25 wt % was deemed to be preferred.

According to an embodiment, the size-distribution of the cross-linked dextran microspheres, as present within the body fluid leakage detection aqueous composition, is such that:
- the volume based mean diameter D[4,3], as determined in accordance with ISO 13 320:2009 by using laser diffraction, is 100 to 1000 µm, such as 250 to 750 m; and/or
- the volume based diameter D[v, 0.9], as determined in accordance with ISO 13 320:2009 by using laser diffraction, is 300 to 2000 µm, such as 500 to 1500 m; and/or
- the volume based diameter D[v, 0.1], as determined in accordance with ISO 13 320:2009 by using laser diffraction, is 50 to 600 µm, such as 100 to 500 µm.

The pH-indicator should be present in an amount sufficient to provide colored composition, at least above, or below, its pKa. Thus, the concentration of the pH-indicator may be at least 0.001 wt %, such as at least 0.005 wt % or 0.01 wt %. Further, seen from a safety perspective, the concentration of the pH-indicator should not be too high. Thus, the concentration of the pH-indicator may be 0.5 wt % or lower, such as 0.25 wt % or 0.1 wt % or lower.

In order to improve the shelf life of the body fluid leakage detection aqueous composition it may further comprise a preservative. Examples of preservative are known to the skilled person and include lactic acid and benzoic acid among others. Given that the composition typically is slightly acidic, the addition of preservative may even be dispensed with.

Further, the body fluid leakage detection aqueous composition may comprise sodium chloride (NaCl) to adjust the tonicity and provide an isotonic composition. In order to provide a buffered, isotonic body fluid leakage detection aqueous composition, phosphate buffered saline (PBS) may be used to dissolve the gelling agent.

According to a preferred embodiment, the body fluid leakage detection aqueous composition is a pancreatic fluid leakage detection aqueous composition. The pH of such a pancreatic fluid leakage detection aqueous composition is in the range 4 to 6. Further, a pKa of the pH-indicator is in the range 6 to 8, such as in the range 6.5 to 7.5. The pH-indicator in the pancreatic fluid leakage detection aqueous composition may be selected from the group consisting of bromothymol blue, phenol red, and neutral red; and preferably the pH-indicator is bromothymol blue.

Such a pancreatic fluid leakage detection aqueous composition may be used in detecting pancreatic fluid leakage in conjunction with pancreatic surgery, e.g. partial pancreatectomy. An embodiment does thus relate to the pancreatic fluid leakage detection aqueous composition for use in detecting pancreatic fluid leakage in conjunction with pancreatic surgery, e.g. partial pancreatectomy. In such use, the pancreatic fluid leakage detection aqueous composition is applied to the pancreas during pancreatic surgery. The pancreatic fluid leakage detection aqueous composition may be applied by means of a syringe. Preferably, the pancreatic fluid leakage detection aqueous composition is applied as a continuous layer on the pancreas. A continuous layer may be provided by applying a string from a syringe in a meandering pattern on the pancreas. The thickness of the applied layer should be as even as possible. A too thick layer may hamper visualization of any leakage.

Based on its properties, the composition will maintain its initial color (yellow if bromothymol blue is used) unless there is leakage of pancreatic fluid. A leakage of pancreatic fluid will locally raise the pH in the composition and result in a local color change (blue to blue-greenish if bromothymol blue is used), not only being indicative for the amount of but also localizing the exact point of leakage. The surgeon is thus being made aware that closure or anastomosis of the pancreatic remnant is insufficient and additional treatment is needed before the abdominal cavity is to be closed or perioperative management has to be changed, e.g. drainage placement, medication or treatment on intensive care unit. Further, the surgeon is also provided with guidance regarding the exact localization of leakage on the tissue surface. The latter is important guidance for targeted the closure treatment; e.g. additional ligature.

A further embodiment of the invention relates to a method of detecting leakage of pancreatic fluid in conjunction with pancreatic surgery. In such method, the pancreatic fluid leakage detection aqueous composition is applied to the pancreas during pancreatic surgery, e.g. after conventional closure of the pancreatic remnant in distal pancreatectomy with ligature treatment, such as transversal non-absorbable single-stitch sutures or stapler usage. As already explained, leakage of pancreatic fluid will be detected and localized on the tissue surface by a change in color of the pancreatic fluid leakage detection aqueous composition applied the surface. The method may comprise a further step of stopping a detected leakage, such as by targeted ligature treatment, e.g. non-absorbable single/x-stitch sutures, or application of staples. As pancreatic fluid leakage detection aqueous composition is applied to the tissue surface by intraabdominal injection it can be used both in open as well as in laparoscopic or robot-assisted surgery.

According to another embodiment, the body fluid leakage detection aqueous composition is a biliary leakage detection aqueous composition. The pH of such a bile leakage detection aqueous composition is in the range 4 to 6. Further, a pKa of the pH-indicator is in the range 6 to 8, such as in the range 6.5 to 7.5. The pH-indicator in the bile leakage detection aqueous composition may be selected from the group consisting of bromothymol blue, phenol red, and neutral red; and preferably is the pH-indicator bromothymol blue.

Such a biliary leakage detection aqueous composition may be used in detecting bile leakage in conjunction with abdominal surgery, e.g. after partial liver resection on benign or malignant diseases, liver trauma or liver transplantation. An embodiment does thus relate to the bile leakage detection aqueous composition for use in detecting bile leakage in conjunction with transsection liver surface, traumatic liver damage or biliodigestive anastomosis. In such use, the biliary leakage detection aqueous composition is applied the tissue surface meaning liver capsula, parenchymal cut surface or biliodigestive anastomosis. Based on its properties, the composition will maintain its initial color (yellow if bromothymol blue is used) unless there is leakage of bile. A leakage of bile will locally raise the pH in the composition and result in a local color change (blue to blue-greenish if bromothymol blue is used), not only being indicative for but also localizing the exact point of biliary leakage. The surgeon is thus being made aware of insufficient closure of the liver remnant or biliodigestive anastomosis and additional treatment is needed before the abdominal cavity is to be closed or perioperative management has to be changed, e.g. drainage placement, medication or treatment on intensive care unit. Further, the surgeon is also provided with guidance regarding the amount of and the exact localization of biliary leakage. The latter is important guidance for targeted closure of the leaking liver tissue surface or biliodigestive anastomosis such as ligature, staple treatment or application of biological or artificial closure patches. As biliary fluid leakage detection aqueous composition is applied to the tissue surface by intra-abdominal injection it can be used both in open as well as in for laparoscopic or robot-assisted surgery. Without further elaboration, it is believed that one skilled in the art may, using the preceding description, utilize the present invention to its fullest extent. The preceding preferred specific embodiments are, therefore, to be construed as merely illustrative and not limitative of the disclosure in any way whatsoever.

Although the present invention has been described above with reference to specific embodiments, it is not intended to be limited to the specific form set forth herein. Rather, the invention is limited only by the accompanying claims and, other embodiments than the specific above are equally possible within the scope of these appended claims, e.g. different than those described above.

In the claims, the term "comprises/comprising" does not exclude the presence of other elements or steps. Additionally, although individual features may be included in different claims or different embodiments, these may possibly advantageously be combined, and the inclusion in different claims or embodiment does not imply that a combination of features is not feasible and/or advantageous.

In addition, singular references do not exclude a plurality. The terms "a", "an", "first", "second" etc. do not preclude a plurality.

BRIEF DESCRIPTION OF THE DRAWINGS

These and other aspects, features and advantages of which the invention is capable of will be apparent and elucidated from the following description of the exemplary embodiments of the present invention, reference being made to the accompanying drawings, in which:

FIG. 1 is sequence of photographs taken during pancreatic surgery (distal pancreatectomy). FIG. 1b) was successful.

EXPERIMENTAL

The following examples are mere examples and should by no means be interpreted to limit the scope of the invention. Rather, the invention is limited only by the accompanying claims.

Material

Of the three different kinds (size and degree of cross-linking) of cross-linked starch microspheres used, two were produced in-house at Magle AB (Kristianstad, Sweden) as described below and the third (Arista®) was obtained from Davol Inc. All other chemicals and reagents used in the making of the cross-linked, starch microspheres and in the succeeding preparations of the hydrogels of analytical grade and obtained VWR International AB unless otherwise noted. The native potato starch was obtained from Lyckeby Starch (Kristianstad, Sweden).

General

In short, cross-linked starch microspheres of the first two types were provided by:

Hydrolyzing native starch to provide shorter polymer chains;

Reducing terminal aldehydes group to avoid reduce discoloration;

Forming an emulsion comprising spherical starch droplets;

Cross-linking the starch in the droplets to provide cross-linked starch microspheres; and cross-linked starch microspheres; and Washing the cross-linked starch microspheres.

The properties of the resulting cross-linked starch microspheres do, as recognized in the art, depend on a number of factors including:

the degree of hydrolysis, i.e. the length of the polymer chains (affected by the pH, reaction time and temperature);

the size of the micro-spheres (affected by the type of emulsifier, the length of the polymer chains and the stirring rate); and the degree of cross-linking (affected by the weight ratio epichlorohydrin:starch).

Preparation of Hydrolyzed Starch (HST) Solution

To a first reactor is charged, purified water under stirring at room temperature. To the first reactor is then charged concentrated hydrochloric acid. To the diluted acid is now charged native potato starch in portions under stirring. The jacketed temperature is raised. The mixture is stirred at the elevated temperature until the desired degree of hydrolysis is achieved. After the reaction time is completed the jacketed temperature is lowered to room temperature. The acidic reaction mixture is quenched by a controlled addition of sodium hydroxide. The inner temperature should not exceed the temperature of the reaction during charged of the base. To the mixture, sodium borohydride is charged under stirring and controlled conditions at room temperature. Once, the borohydride is dissolved completely the mixture is stirred for a complete reaction to occur.

Preparation of Microspheres

To the second reactor, toluene and RHODAFAC® PA17 emulsifier are charged under controlled condition and stirred at elevated temperature until the RHODAFAC® PA17 emulsifier is completely dissolved. To the second reactor is now charged the content of the first reactor, comprising hydrolyzed and reduced native starch, at a high stirring rate until a stable suspension obtained. The stirring rate and thereby the composition of the suspension is adjusted depending on which range of microspheres that is to be produced. To the suspension, epichlorohydrin is charged under controlled conditions. The amount of the cross-linker charged is depending on which range of microspheres that is to be produced. The reaction is kept overnight at the elevated temperature. Ethanol is charged and jacketed temperature is lowered down to room temperature, and the crude product sediments. The clear top phase is siphoned off.

Work-Up

Ethanol is charged to the crude product under stirring. Once homogeneous, the mixture then allowed to sediment. The top phase is siphoned off. This sequence is repeated three times.

To the product mixture is charged purified water, under stirring. To the slurry is now charged acetic acid, under stirring to obtain pH 4-5. The, ethanol is charged. Once homogeneous, the mixture is allowed to sediment and then the top phase is siphoned off.

To the reactor is charged a pre-made aqueous solution of ethanol (20 wt. %), the mixture is stirred. Once homogeneous, the mixture is allowed to sediment and then the top phase is siphoned off. This sequence is repeated four times.

Repeat the above procedure without sedimentation, but, the mixture is collected from the bottom valve and filtrated.

The product is rinsed with absolute ethanol and filtered. The rinse procedure is repeated for five times.

The product is dried in a stainless-steel tray at 60° C. under vacuum, and sieved through 400 micron sieve (first type) to provide microspheres in the size range (wet state; dispersed in purified water) of 32 to 900 µm, or through a 600 micron sieve (second type) to provide microspheres in the size range (wet state; dispersed in purified water) of 50 to 1200 µm.

Types of Microspheres

By use of this method, two types of cross-linked starch micro-spheres were produced. The first type having a volume based mean diameter (D[4,3]) of about 450 µm (wet state; dispersed in purified water) and degree of cross-linking of about 14%. The second type having volume based mean diameter (D[4,3]) of about 620 µm (wet state; dispersed in purified water) and degree of cross-linking of about 15% were produced.

As already stated, the third type of microspheres were Arista® provided by Davol Inc. These microspheres have volume based mean diameter (D[4,3]) of about 138 µm (wet state; dispersed in purified water) and degree of cross-linking of about 11%.

Provision of Pancreatic Fluid Leakage Detection Composition

In order to provide a pancreatic fluid leakage detection composition, native potato starch (cf. example 21 and 22), microspheres (15 g) of the first, second or third type was charged to an ethanol solution 25 ml containing bromothymol blue (0.2% w/w). The resulting mixture was stirred for 30 minutes at room temperature, upon which the mixture was dried under vacuum at 60° C. over-night.

The dried product, stem mixture (15 g) was dissolved in 100 ml of purified water, or pre-made solution containing saline and a phosphate buffer, and optional acidified by addition of hydrochloric acid. The mixture was stirred until a homogeneous solution was obtained at room temperature, then the homogeneous stem gel was then filled on syringes.

Using this protocol, 25 pancreatic fluid leakage detection compositions were obtained. Modifications to this protocol as well as the type of microspheres to provide each example is indicated below.

Example 1

Stem mixture comprising microspheres of the third type is charged to purified water, 100 ml and acidified with hydrochloric acid (0.1 M). The homogeneous gel was then filled on syringes.

Example 2

Stem mixture comprising microspheres of the second type is charged to purified water, 100 ml without any acidification. The homogeneous gel was then filled on syringes.

Example 3

Stem mixture comprising microspheres of the third type is charged to purified water, 100 ml and acidification by 5 ml hydrochloric acid (0.1 M). The homogeneous gel was then filled on syringes.

Example 4

Stem mixture comprising microspheres of the second type is charged to a pre-made solution containing saline, 83 ml and a phosphate buffer at pH 6.4, 1 ml. The pH of the resulting gel was adjusted to 4.5 using 0.1 M hydrochloric acid. The mixture was stirred until a homogeneous slurry is obtained. The homogeneous gel was then filled on syringes.

Example 5

Stem mixture (20.5 g) comprising microspheres of the second type was charged to a pre-made solution containing saline, 100 ml. The solution is acidified by use of hydrochloric acid, 0.1 M. The mixture is stirred until a homogeneous slurry is obtained. The homogeneous gel is then filled on syringes.

Example 6

Stem mixture (29.5 g) comprising microspheres of the second type, is charged to a pre-made solution containing saline, 150 ml. The solution is adjusted to 4.5 by use of hydrochloric acid, 1 M. The mixture is stirred until a homogeneous slurry is obtained. The homogeneous gel is then filled on syringes.

Example 7

Stem mixture comprising microspheres of the second type, is charged to a pre-made solution containing saline, 85 ml and a phosphate buffer 1 M at pH 5.8, 1.13 ml. The solution is adjusted to 4.6 by use of hydrochloric acid, 1 M. The mixture is stirred until a homogeneous slurry is obtained. The homogeneous gel is then filled on syringes.

Example 8

Stem mixture comprising microspheres of the second type, is charged to a pre-made solution containing saline, 85 ml and a phosphate buffer 1 M at pH 5.8, 1.13 ml. The solution is adjusted to 5.0 by use of hydrochloric acid, 1 M. The mixture is stirred until a homogeneous slurry is obtained. The homogeneous gel is then filled on syringes.

Example 9

Stem mixture comprising microspheres of the second type, is charged to a pre-made solution containing saline, 85 ml and a phosphate buffer 1 M at pH 5.8, 1.13 ml. The solution is adjusted to 4.3 by use of hydrochloric acid, 1 M. The mixture is stirred until a homogeneous slurry is obtained. The homogeneous gel is then filled on syringes.

Example 10

Stem mixture comprising microspheres of the second type, is charged to a pre-made solution containing saline, 85 ml and a phosphate buffer 1 M at pH 5.8, 0.565 ml. The solution is adjusted to 4.5 by use of hydrochloric acid, 1 M. The mixture is stirred until a homogeneous slurry is obtained. The homogeneous gel is then filled on syringes.

Example 11

Stem mixture comprising microspheres of the second type, is charged to a pre-made solution containing saline, 85 ml and a phosphate buffer 1 M at pH 5.8, 0.565 ml. The solution is adjusted to 4.8 by use of hydrochloric acid, 1 M. The mixture is stirred until a homogeneous slurry is obtained. The homogeneous gel is then filled on syringes.

Example 12

Stem mixture comprising microspheres of the second type, is charged to a pre-made solution containing saline, 85 ml and a phosphate buffer 1 M at pH 5.8, 2.26 ml. The solution is adjusted to 4.1 by use of hydrochloric acid, 1 M. The mixture is stirred until a homogeneous slurry is obtained. The homogeneous gel is then filled on syringes.

Example 13

Stem mixture comprising microspheres of the second type, is charged to a pre-made solution containing saline, 85 ml and a phosphate buffer 1 M at pH 5.8, 2.26 ml. The solution is adjusted to 4.7 by use of hydrochloric acid, 1 M. The mixture is stirred until a homogeneous slurry is obtained. The homogeneous gel is then filled on syringes.

Example 14

Stem mixture comprising microspheres of the second type, is charged to a pre-made solution containing saline, 83 ml and a phosphate buffer 1 M at pH 5.8, 0.1 ml. The pH of the gel is adjusted to 5.8 using 1 M hydrochloric acid. The mixture is stirred until a homogeneous slurry is obtained. The homogeneous gel is then filled on syringes and sterilized in an autoclave.

Example 15

Stem mixture comprising microspheres of the second type, is charged to a pre-made solution containing saline, 83 ml and a phosphate buffer 1 M at pH 5.8, 0.457 ml. The pH of the gel is adjusted to 4.7 using 1 M hydrochloric acid. The mixture is stirred until a homogeneous slurry is obtained. The homogeneous gel is then filled on syringes and sterilized in an autoclave.

Example 16

Stem mixture comprising microspheres of the second type, is charged to a pre-made solution containing saline, 83 ml and a phosphate buffer 1 M at pH 5.8, 0.125 ml. The pH of the gel is adjusted to 4.5 using 0.1 M hydrochloric acid. The mixture is stirred until a homogeneous slurry is obtained. The homogeneous gel is then filled on syringes and steam sterilized in an autoclave.

Example 17

Stem mixture, 48 g comprising microspheres of the second type, is charged to a pre-made solution containing saline, 230 ml and a phosphate buffer 1 M at pH 5.8, 0.345 ml. The pH of the gel is adjusted to 4.6 using 1 M hydrochloric acid. The mixture is stirred until a homogeneous slurry is obtained. The homogeneous gel is then filled on syringes.

Example 18

Stem mixture, 48 g comprising microspheres of the second type, is charged to a pre-made solution containing saline, 230 ml and a phosphate buffer 1 M at pH 5.8, 0.345 ml. The pH of the gel is adjusted to 4.6 using 1 M hydrochloric acid. The mixture is stirred until a homogeneous slurry is obtained. The homogeneous gel is then filled on syringes and steam sterilized in an autoclave.

Example 19

Stem mixture, 31 g comprising microspheres of the second type, except the size range (wet state; dispersed in purified water) of the microspheres being 150 to 2000 µm, is charged to a pre-made solution containing saline, 140 ml and a phosphate buffer 1 M at pH 5.8, 0.21 ml. The pH of the gel is adjusted to 4.6 using 1 M hydrochloric acid. The mixture is stirred until a homogeneous slurry is obtained. The homogeneous gel is then filled on syringes.

Example 20

Stem mixture, 28 g comprising microspheres of the second type, except the size range (wet state; dispersed in purified water) of the microspheres being 150 to 1600 µm, is charged to a pre-made solution containing saline, 130 ml and a phosphate buffer 1 M at pH 5.8, 0.195 ml. The pH of the gel is adjusted to 4.5 using 1 M hydrochloric acid. The mixture is stirred until a homogeneous slurry is obtained. The homogeneous gel is then filled on syringes.

Example 21

Stem mixture, 10 g comprising native potato starch is charged to a pre-made solution containing saline, 120 ml, glycerol 4.4 g and a phosphate buffer 1 M at pH 5.8, 0.075 ml. The mixture was heated to 70° C. and stirred for 30 minutes. The pH of the gel is adjusted to 4.5 using 0.1 M hydrochloric acid. The mixture is stirred until a homogeneous slurry is obtained. The homogeneous gel is then filled on syringes.

Example 22

Stem mixture, 10 g comprising native potato starch is charged to a pre-made solution containing saline, 120 ml, glycerol 4.4 g and a phosphate buffer 1 M at pH 5.8, 0.05 ml. The mixture was heated to 70° C. and stirred for 30 minutes. The pH of the gel is adjusted to 4.5 using 0.1 M hydrochloric acid. The mixture is stirred until a homogeneous slurry is obtained. The homogeneous gel is then filled on syringes.

Example 23

Stem mixture comprising microspheres of the first type, is charged to a pre-made solution containing saline, 87 ml, and a phosphate buffer 1 M at pH 5.8, 0.124 ml. The mixture was heated to 70° C. and stirred for 30 minutes. The pH of the gel is adjusted to 4.4 using 0.1 M hydrochloric acid. The mixture is stirred until a homogeneous slurry is obtained. The homogeneous gel is then filled on syringes.

Example 24

Stem mixture comprising microspheres of the first type, is charged to a pre-made solution containing saline, 87 ml, and a phosphate buffer 1 M at pH 5.8, 0.124 ml. The mixture was heated to 70° C. and stirred for 30 minutes. The pH of the gel is adjusted to 4.4 using 0.1 M hydrochloric acid. The mixture is stirred until a homogeneous slurry is obtained. The homogeneous gel is then filled on syringes.

Example 25

Stem mixture comprising microspheres of the first type, is charged to a pre-made solution containing saline, 83 ml, and a phosphate buffer 1 M at pH 5.8, 0.124 ml. The mixture was heated to 70° C. and stirred for 30 minutes. The pH of the gel is adjusted to 4.6 using 0.1 M hydrochloric acid. The mixture is stirred until a homogeneous slurry is obtained. The homogeneous gel is then filled on syringes.

In Vitro Evaluation

The obtained body fluid leakage detection aqueous compositions (i.e. examples 1 to 25) were evaluated in vitro using saliva-moistened filter-paper, fresh porcine pancreatic tissue, and fresh human pancreatic fluid. Porcine pancreatic tissue was donated by regional slaughterhouse (Fleischversorgungszentrum Mannheim) and stored at 2° C. temperature until experimental usage within 12 hours post mortem. Human pancreatic fluid was aspired from fresh surgical specimen of patients after informed consent in accordance to the Declaration of Helsinki (approved by Heidelberg University ethics committee; votes 301/2001, 159/2002). In vitro methods provided highly controlled testing with limited complexity. Thus, the samples could be evaluated quickly on a) practicability of usage, b) time to reaction, c) clarity and d) preciseness of indication and immediate feedback to the developers enabled for rapid optimization of the indicator.

In the in vitro testing, some conclusions could be drawn:

It was found that a degree of cross-linking of around 12.5 wt % (cf. example 3) was a bit too low to provide optimum properties, as the composition seemingly was degraded quite rapidly. Increasing the degree of cross-linking to about 16 wt % (cf. examples 2, 11, 14, 16, and 17) provided the composition with proper resistance to amylase degradation by pancreatic juice (i.e. being stable for at least 5 minutes);

The amount of microspheres in the composition affects the viscosity of the composition. It was concluded that less than 10 wt % microspheres (cf. examples 21 and 22) provided too liquid compositions to provide optimum properties, whereas 20 wt % microspheres or more (cf. example 5) provided a too thick composition to provide optimum properties. A concentration of 13 to 18 wt % microspheres (cf. examples 1, 2, 6-20, 23, and 24) provided a composition being easy to handle and providing quick, i.e. within 5 minutes, and precise leakage detection;

It is preferred to keep the concentration of the pH indicator as low as possible. It should however be sufficiently high to provide clearly visible leakage detection. A concentration of BTB lower than 0.04 wt % (cf. examples 1 and 2) provided somewhat weak colors, though still visible; and Compositions not being buffered provided less precise leakage detection. Further, composition with high buffer strength (cf. examples 5-9, 12 and 13) provided somewhat slow detection, whereas a buffer strength of 1 to 10 mM (cf. examples 10, 11 and 14 to 24) provided a quick and precise leakage detection.

In Vivo Verification

Based on the in vitro evaluation, selected body fluid leakage detection aqueous compositions (i.e. example 1-25) were evaluated in animal model as well. Animal trial project was approved by regional administrative authority (Regierungspräsidium Karlsruhe according to Deutsches TierSchG (German animal law) § 8 Abs. 1, reference number 35-9835.81/G-184/16) for indicator development and testing on domestic pigs (*Sus scrofa domestica*) undergoing pancreatic surgery. Surgery was conducted under general anesthesia as used in human.

In a first proof of concept experiment (n=10 animals) preliminary body fluid leakage detection aqueous compositions (example 1-5) were tested on their technical applicability and performance in final pancreatic operations (distal pancreatectomy, DP, see below). Parallel to in vitro experiments the characteristics a) practicability of usage, b) time to reaction, c) clarity and d) preciseness of indication were evaluated followed by evaluation of initial tissue damage caused by the indicator using postoperative histological analysis of the pancreatic stump.

The second experiment (n=8 animals) consisted of initial distal pancreatectomy (cf. below) followed by 48 hours of observation of local cytotoxicity and systemic side effects of the body fluid leakage detection aqueous compositions (example 5-25) and terminal reoperation with evaluation of intra-abdominal pathologies and retrieval of tissue samples for histological analysis. Following a three-armed study-design animals were divided into an indicator-negative group with no leakage detected and if indicator detected leakage randomly subdivided into an indicator-positive group with no extra closure and an indicator-positive group with targeted extra-closure. Thus, sensitivity and specificity, as well as impact of refined closure of postoperative pancreatic fistula, could be studied. During observation, short-term impact of body fluid leakage detection aqueous composition use on biological organism was observed by clinical evaluation complemented by laboratory analysis of blood and peritoneal fluid samples. Clinical parameters included signs of infection or postoperative pancreatic fistula, blood analysis included markers of inflammation, anemia, or pancreatitis in the blood as well as pancreatic leakage in peritoneal fluid.

Experiment number three (n=16 animals) was conducted analog to the second experiment but observational time was extended to 8 days to make evaluation of mid- to long-term impact of body fluid leakage detection aqueous composition use on biological organism possible. Based on clinical-knowledge it is known that within this time almost all postoperative pancreatic fistula become clinically apparent. On the opposite if no complication occurs one week after the operation can be seen as average time point of discharge from hospital which sets the major timeframe for clinical management.

Distal Pancreatectomy (DP)

The abdominal cavity was opened by median laparotomy and the omental bursa was open to expose the pancreas. Once exposed, the last 2 to 3 cm of the pancreas (porcine splenic lobe) was surgically released from surrounding peritoneal tissue and the distal 2 cm of the pancreas was resected with scalpel. Bleeding was stopped with single/x-stitch non-absorbable sutures (max. 3 per animal). Closure of the pancreatic remnant was conducted with transversal non-absorbable single-stitch sutures (lx/cm surface). Thereafter the closed pancreatic stump was rinsed and cleaned with saline.

Once rinsed, a body fluid leakage detection aqueous composition according to above was applied to the whole surface of the pancreatic stump. The composition appears yellow when applied, but will locally turn green-bluish if pancreatic juice is leaking due to insufficient closure at some localization. This indicator reaction happens immediately, i.e. within seconds. Given the viscosity of the composition the color change only appears in close proximity to the leakage.

In case of leakage of pancreatic juice, fine-closure of the stump using non-absorbable single/x-stitch sutures can be applied over visualized leaks. Thereafter the closure can be controlled by unlimited repetition of application of the composition. Eventually, the composition gel was removed with gauze and saline rinsing. An abdominal silicone drainage was placed next to the pancreatic stump for postoperative evacuation and analysis of fluid; and the abdominal wall was closed.

Toxicology and Cytotoxity

PAN toxicology was evaluated by analyzing in vivo pharmacokinetics of its degradation products over 48 hours. Additionally, acute local tissue injury caused by the indicator within minutes as well as macroscopic intra-abdominal side effects and local histological of the device over 8 days were assessed. Finally, cytotoxicity of its degradation products on pancreatic target cells was analyzed.

For toxicological evaluation of PAN indicator hydrogel pharmacokinetics studies were conducted measuring concentrations of degradation products of the device in body fluid components over time consequently to abdominal application in pancreatic surgery. Blood from portal vein and peritoneal fluid from intraoperative situs or postoperative drainages were sampled. Time points of sampling in relation to indicator application were: 0 min (baseline before indicator application), 1, 5, 30, 60, and 120 min, $1^{st}$ and $2^{nd}$ postoperative day. Due to its composition with water and degradable components starch microspheres, only further constituent bromothymol blue (BTB) needed to be evaluated. It should be evaluated if and how much BTB stays in the organism after application at the pancreatic surgery field, gets resorbed to portal venous circulation and passes liver metabolism to reach central venous circulation. Thus, samples of body were collected at the different body compartments over time as described above. Due to expected extremely small BTB-amounts to be measured the very sensitive detection method High Pressure Liquid Chromatography-Mass Spectrometry (HPLC-MS) was used.

In all pigs an immediate and strong increase of BTB-concentration in drainage fluid after indicator application was followed by gradual decrease with small detectable BTB-amounts on $1^{st}$ postoperative day (<20 ng/ml) until on $2^{nd}$ postoperative day there was no detectable amount of BTB left in any of the pig's drainage fluid. In portal venous blood, small amounts of BTB were found only in one pig 5 and 30 minutes after application. In the remaining pigs and timepoints no BTB was detected (Table 1).

TABLE 1

| BTB-Concentration in drainage and Portal Venous Blood, respectively | | | | | | | | |
| --- | --- | --- | --- | --- | --- | --- | --- | --- |
| Animal No. | Min 0 | Min 1 | Min 5 | Min 30 | Min 60 | Min 120 | Day 1 | Day 2 |
| Drainage BTB-Concentration at Time Point [ng/ml] | | | | | | | | |
| Tox 1 | 0 | 2060 | 7650 | 3280 | 1140 | 619 | 32.1 | — |
| Tox 2 | 0 | 9220 | 389 | 10.7 | 9.27 | 263 | 18.9 | 0 |
| Tox 3 | 0 | 3600 | 2560 | 1220 | 1270 | 631 | 14.4 | 0 |
| Tox 4 | 7.44 | 2010 | 2070 | 712 | 224 | 121 | 2.98 | 0 |
| Mean | 1.9 | 4222.5 | 3167.3 | 1305.7 | 660.8 | 408.5 | 17.1 | 0 |

TABLE 1-continued

BTB-Concentration in drainage and Portal Venous Blood, respectively

| Animal No. | Min 0 | Min 1 | Min 5 | Min 30 | Min 60 | Min 120 | Day 1 | Day 2 |
|---|---|---|---|---|---|---|---|---|
| Portal Venous Blood BTB-Concentration at Time Point [ng/ml] | | | | | | | | |
| Tox 1 | 0 | 0 | 0 | 0 | 0 | 0 | 0 | 0 |
| Tox 2 | 0 | 0 | 0 | 0 | 0 | 0 | 0 | 0 |
| Tox 3 | 0 | 0 | 0 | 0 | 0 | 0 | 0 | 0 |
| Tox 4 | 0 | 0 | 2.02 | 2.11 | 0 | 0 | 0 | 0 |
| Mean | 0 | 0 | 0.51 | 0.53 | 0 | 0 | 0 | 0 |

To check short-term local histopathological changes in pancreas caused by the indicator, a total of 24 fresh pancreatic tissue specimens from six pigs were harvested for histopathological evaluation. Four transversal slices with equal size (2 cm) were harvested from each pig and were treated with PAN or saline (control) for 5 or 10 minutes. After 5 or 10 minutes the indicator was flushed away, and the pancreatic tissues were immediately fixed and set in paraffin blocks for histological evaluation.

Histology showed no significant local damage, pancreatitis or cytotoxicity. No differences in histopathological score for acute pancreatic injury was observed between treatment and control groups.

Cytotoxicity by PAN was further evaluated in a cell culture assay. Metabolic activity of viable cells was evaluated by fluorescence photometry of metabolized resofurin from resazurin after incubation with increasing amount of BTB. PAN indicator hydrogels contain BTB at a concentration of almost 0.5 mg/ml. Thus BTB-solutions with concentrations of 0.5 mg/ml, 1 mg/ml, 1.5 mg/ml, and 5.5 mg/ml, respectively were tested. Cytotoxicity is defined as cell viability less than 70%. No cytotoxicity was observed for 0.5-1.5 mg/ml of BTB. 5.5 mg/ml of BTB showed slight toxicity.

Comparison: Indicator(+)/Extra Suture, Indicator(+)/No Extra Suture, and Indicator(−)

Impact of indicator-based targeted closure of the pancreatic remnant to reduce pancreatic fistula rate was evaluated by investigation of p-amylase and p-lipase levels in the drainage fluid.

The indicator was tested after distal pancreatectomy in living pigs. The pigs were divided into study groups according to the indicator reaction visualizing leakage out of the standard-closed pancreatic remnant as "indicator negative/positive". In case of "positive" indicator-reaction animals were sub grouped randomly into those who received an indicator-based targeted closure ("extra suture") or those who did not receive any extra closure of the visualized leakage. Randomization was conducted by toss of a coin.

Group 1: Indicator positive, no extra suture;
Group 2: Indicator positive, extra suture; and
Group 3: Indicator negative In order to assess the effect of the targeted closure, α-amylase and lipase were measured in the serum and drainage at day 0-8 (cf. result presented in FIGS. 2 and 3). Elevated concentrations of pancreatic enzymes in abdominal cavity/ascites postoperatively represent occurrence and intensity of biochemical leakage of pancreatic secretions that can lead to postoperative pancreatic fistula. Values at day 0 represent baseline conditions, while following values indicate postoperative course. According to international definitions, from day three after the operation enzyme levels must have dropped below 3 times upper limit institutional normal serum values to rule out existence of biochemical leak. If clinical manifestations add to an existing biochemical leak a postoperative pancreatic fistula can be diagnosed in accordance to the definition.

Figure 1A:
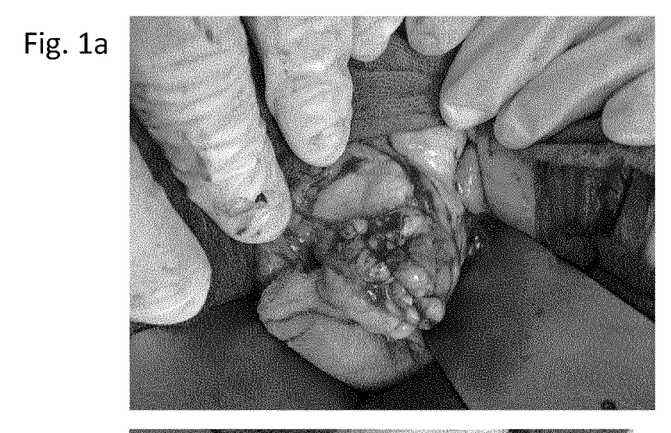
FIG. 1a depicts the closed part of pancreas remaining after distal pancreatectomy. No leakage is apparent to the bare eye. However, as can be seen in FIG. 1b leakage was still visualized (cf. arrows) by means of the present body fluid leakage detection aqueous composition.
Figure 1B:
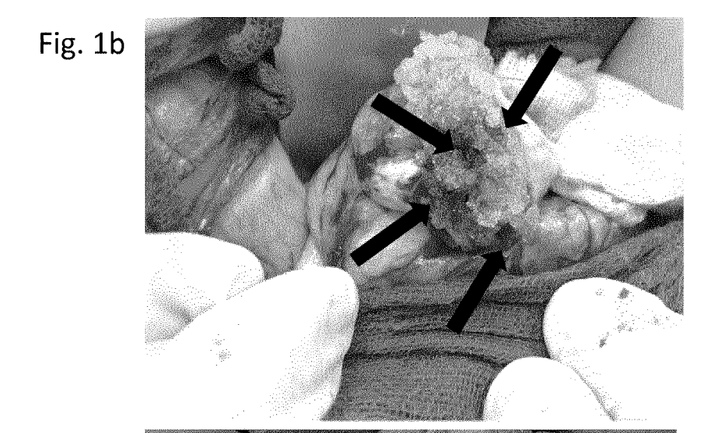
Figure 1C:
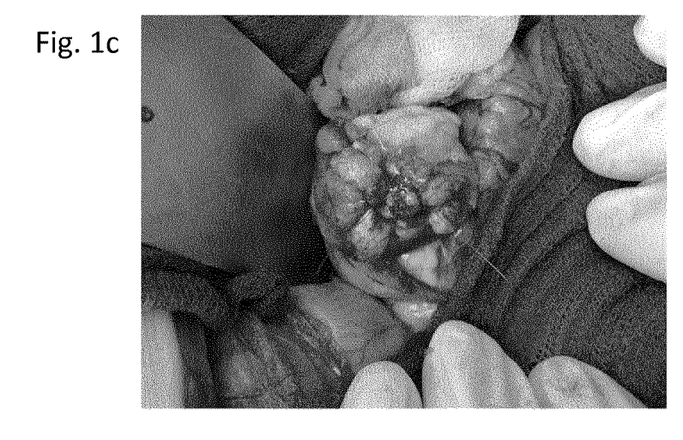
FIG. 1c depicts pancreas after targeted closure of localized leakage. Finally, as can be seen in FIG. 1d, re-application of the present body fluid leakage detection aqueous composition confirmed that the targeted closure of localized leakage (cf.
Figure 1D:
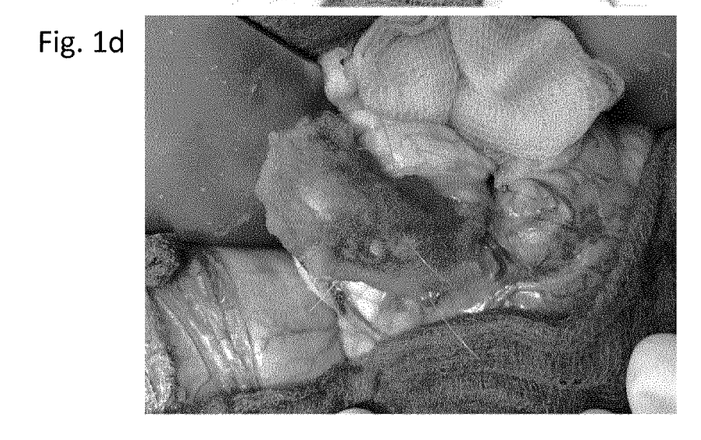
Figure 2:
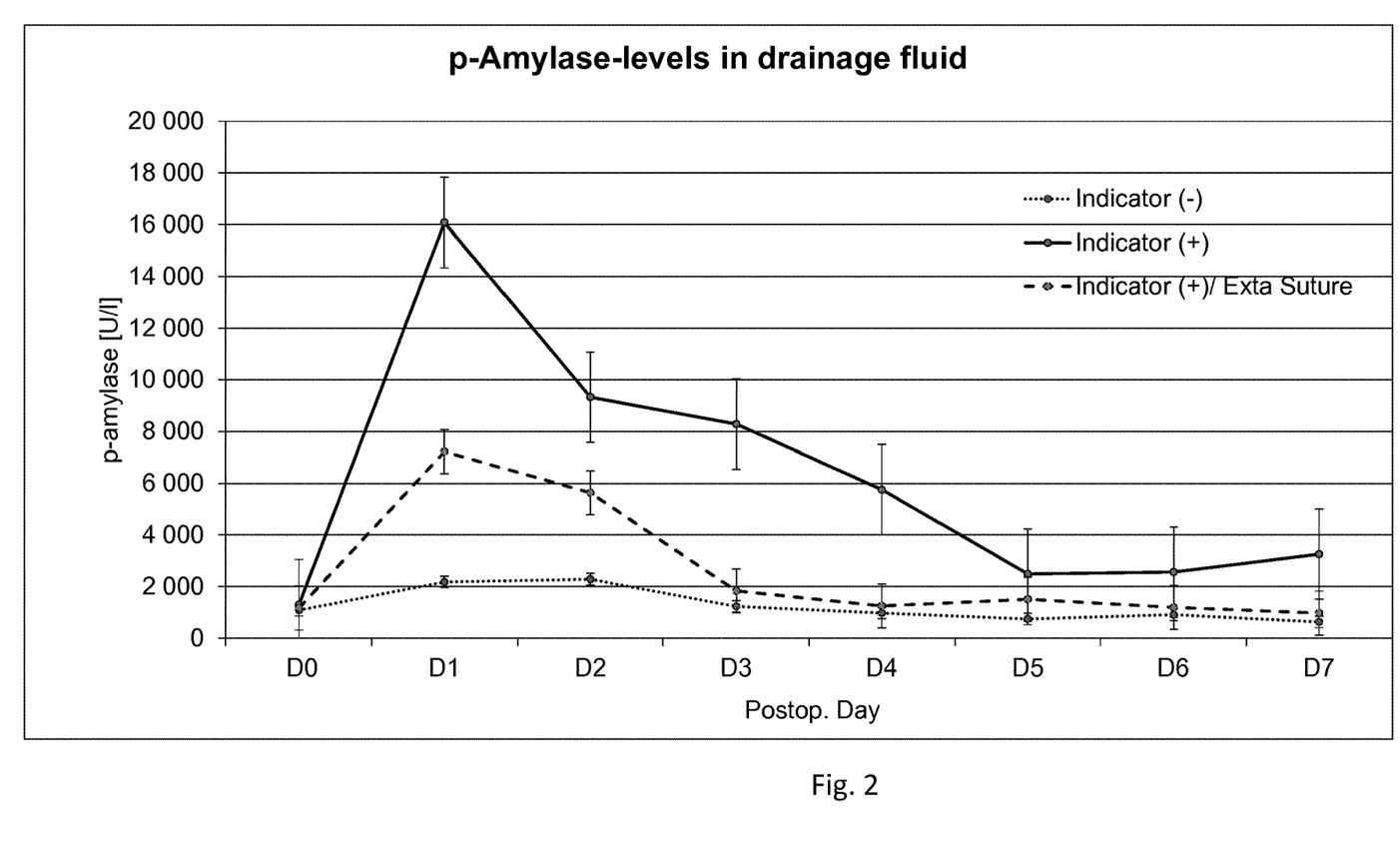
FIG. 2 shows the p-amylase levels directly after pancreatic surgery (DO) and up to D7 (with and without extra sutures after having detected leakage of pancreatic fluid)
Figure 3:
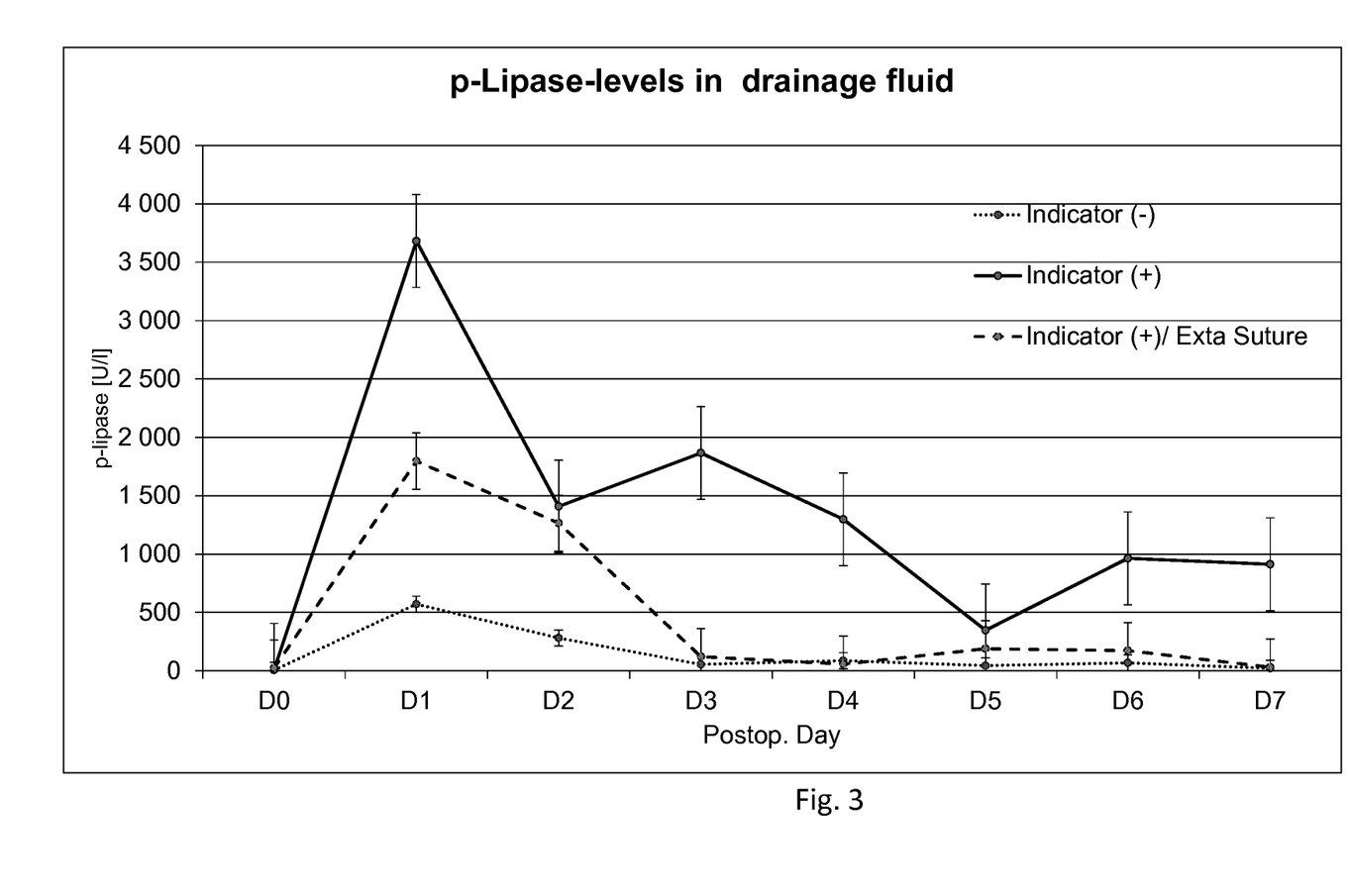
FIG. 3 shows the lipase levels in the different animal groups right after and up to day 7 following pancreatic surgery (with and without extra sutures after having detected leakage of pancreatic fluid).

After the surgery concentration of pancreatic enzymes in abdominal drainages differed significantly between the treatment groups. There was a large elevation of amylase levels of treatment group 1 (indicator positive, no extra treatment) as compared to treatment group 3 (indicator negative) (FIG. 2). Over the following days 5-day 7 elevation tendency remained, though gradually decreasing. Interestingly, variation of concentration levels in group 1 (indicator positive, no extra treatment) was high with standard deviation >10 000 U/l on day 1 and >5 000 U/l on day 2, day 3, day 5, and day 7. Variation in group 2 (indicator positive, extra suture) and especially in group 3 (indicator negative) was much smaller with standard deviations always <3500 U/l and <1500 U/l, respectively.

Targeted closure in treatment group 2 (indicator positive, extra suture) led to definite reduction of drainage fluid enzyme levels as compared to treatment group 1 (indicator positive, no extra treatment). Reduction of drainage enzyme levels was so distinctive that a significant difference could no longer be seen if group 2 (indicator positive, extra treatment) and group 3 (indicator negative) were compared (p>0.05 for all postoperative days).

Drainage lipase values were analyzed from day 0-7. Lipase has been shown to, in addition to amylase, be an early indicator of pancreatic leakage. As expected, drainage lipase levels developed parallel (cf. FIG. 2) to drainage amylase levels correlating with pancreatic leakage. In accordance with results of amylase levels there were much higher levels of lipase in drainages in treatment group 1 (positive, no extra treatment), as compared to group 3 (negative), while a reduction was seen in group 2 (positive, extra suture).

CONCLUSIONS

A novel in vitro body fluid leakage detection aqueous composition was developed. The body fluid leakage detection aqueous composition was evaluated and adapted in vivo to finally be easily applicable on pancreatic remnant or anastomotic tissue as a fast reacting body fluid leakage detection aqueous composition. Proof of concept showed that the composition visualizes pancreatic leakage precisely and fast on the resection margin in a porcine model of distal pancreatectomy.

Sensitivity and specificity of the composition towards pancreatic leakage were both 100%. Visual resolution was smaller than one droplet (<500 μm diameter). Thus, refined targeted leak-closure followed by tightness-control through unlimited indicator-reapplication became possible.

In mid- to long-term observational porcine studies, the composition did not harm the organism significantly. Importantly, no systemic side effects occurred. At the pancreas, the composition did not lead to significant pancreatitis, bleeding or cytotoxicity as confirmed by histology. Detected pancreatic leakage visualized by positive indicator reaction specifically led to postoperative pancreatic fistula in all cases, which was not only confirmed by increased concentrations of pancreatic enzymes in peritoneal fluids within the first days after the operation, but also accompanied by specific medical conditions like delayed gastric-emptying or intra-abdominal abscess. On the opposite targeted leak-closure to reduced postoperative pancreatic fistula-rate significantly as seen by enormous reduction of levels of pancreatic enzymes in peritoneal fluid followed by quick recovery of the animals.

This body fluid leakage detection aqueous composition visualizes pancreatic leaks in experimental pancreatic operations easily and fast without relevant side effects or toxicity and allows quantification and precise localization of pancreatic leakage directly within the operation. Visualization enables adapted perioperative management as well as targeted closure of leakage significantly reducing occurrence of postoperative pancreatic fistula.

Further, the body fluid leakage detection aqueous composition has been confirmed to be safe, i.e. not associated it any significant cytotoxicity effect. Furthermore, it has been verified that the gel may contribute to lower the postoperative risk after pancreatic surgery.

The invention claimed is:

1. A body fluid leakage detection aqueous composition, wherein the composition is a pancreatic fluid leakage detection aqueous composition, the composition comprising a gelling agent, increasing the viscosity of the composition, wherein the gelling agent is cross-linked α-glucan microspheres, and buffering species, the composition thereby being buffered, wherein the composition further comprises a pH-indicator selected from the group consisting of bromothymol blue, phenol red, anthocyanins, and neutral red, wherein the pH of the composition is at least 0.1 pH units lower than a pKa of the pH-indicator, wherein the pH of the composition is in the range of 4 to 6, and wherein the pKa of the pH-indicator is in the range of 6 to 8.

2. The body fluid leakage detection aqueous composition according to claim 1, wherein the gelling agent is cross-linked starch microspheres or cross-linked dextran microspheres.

3. The body fluid leakage detection aqueous composition according to claim 2, wherein the composition comprises 5 to 25 wt % cross-linked starch microspheres or cross-linked dextran microspheres.

4. The body fluid leakage detection aqueous composition according to claim 3, wherein the degree of cross-linking, expressed as the weight ratio cross-linker:starch, or as ratio cross-linker:dextran, is in the range 12 to 20 wt %.

5. The body fluid leakage detection aqueous composition according to claim 3, wherein a volume based mean diameter (D[4,3]), as determined in accordance with ISO 13 320:2009 by using laser diffraction, of the cross-linked starch microspheres, or the cross-linked dextran microspheres, as present in the composition, is 100 to 1000 μm.

6. The body fluid leakage detection aqueous composition according to claim 1, wherein the pH of the composition is at least 0.2 pH units lower than the pKa of the pH-indicator.

7. The body fluid leakage detection aqueous composition according to claim 1, wherein the pH-indicator is bromothymol blue.

8. The body fluid leakage detection aqueous composition according to claim 1, wherein the pH of the composition is between 5 and 6.

9. The body fluid leakage detection aqueous composition according to claim 1, wherein the buffering species being present in an amount of 0.1 to 30 mM.

10. The body fluid leakage detection aqueous composition according to claim 9, wherein the composition is phosphate buffered.

11. The body fluid leakage detection aqueous composition according to claim 1, wherein the composition comprises:
   13 to 17 wt % of the gelling agent, the gelling agent being cross-linked starch microspheres, the cross-linked starch microspheres being cross-linked by epichlorohydrin;
   0.005 to 0.25 wt % of the pH-indicator, the pH-indicator being bromothymol blue;
   at least 75 wt % water; and
   optionally phosphate buffered saline; wherein:
   the cross-linked starch microspheres have a degree of cross-linking of 13.5 to 18.5 wt %; and
   the buffer concentration is 0.5 to 10 mM.

12. The body fluid leakage detection aqueous composition according to claim 1, wherein the aqueous composition further comprises:
   a preservative; and/or
   saline.

13. The body fluid leakage detection aqueous composition according to claim 1, wherein the pKa of the pH-indicator is in the range 6.5 to 7.5.

14. The body fluid leakage detection aqueous composition according to claim 1, wherein the pancreatic fluid leakage detection aqueous composition is for use in detecting pancreatic fluid leakage in conjunction with pancreatic surgery.

15. A method for detecting pancreatic fluid leakage in conjunction with pancreatic surgery, the method comprising:
   applying a pancreatic fluid leakage detection aqueous composition to a tissue surface of the pancreas during pancreatic surgery, wherein the composition comprises a gelling agent, increasing the viscosity of the composition, wherein the gelling agent is cross-linked α-glucan microspheres, and buffering species, the composition thereby being buffered, wherein the composition further comprises a pH-indicator, wherein the pH of the composition is at least 0.1 pH units lower than a pKa of the pH-indicator, wherein the pH of the composition is in the range 4 to 6, and wherein the pKa of the pH-indicator is in the range 6 to 8; and
   detecting and localizing any leakage of pancreatic fluid on the tissue surface of the pancreas by a change in color of the pancreatic fluid leakage detection aqueous composition.

16. The method for detecting pancreatic fluid leakage in conjunction with pancreatic surgery according to claim 15, wherein the pancreatic fluid leakage detection aqueous composition is applied after closure of the pancreatic remnant in distal pancreatectomy with ligature treatment.

17. The method for detecting pancreatic fluid leakage in conjunction with pancreatic surgery according to claim 15, wherein the method further comprises the step of:
   stopping a detected leakage.

18. The method for detecting pancreatic fluid leakage in conjunction with pancreatic surgery according to claim 17, wherein the leakage is stopped by ligature treatment or by application of staples.

19. The body fluid leakage detection aqueous composition according to claim 7, wherein the composition comprises 0.001 to 0.5 wt % of bromothymol blue.

20. The body fluid leakage detection aqueous detection composition according to claim 11, wherein the composition comprises:
- 14 to 16 wt % of the gelling agent, the gelling agent being cross-linked starch microspheres, the cross-linked starch microspheres being cross-linked by epichlorohydrin;
- 0.01 to 0.1 wt % of the pH-indicator, the pH-indicator being bromothymol blue;
- at least 75 wt % water; and
- phosphate buffered saline; wherein:
- the cross-linked starch microspheres have a degree of cross-linking of 15.0 to 17.0 wt %; and
- the buffer concentration is 1.0 to 5 mM.

* * * * *